(12) United States Patent
Zhou et al.

(10) Patent No.: US 9,462,955 B2
(45) Date of Patent: Oct. 11, 2016

(54) AUTOMATED IDENTIFICATION OF CULPRIT CORONARY ARTERY USING ANATOMICALLY ORIENTED ECG DATA DISPLAY

(75) Inventors: Sophia Huai Zhou, Camarillo, CA (US); Alejo Costa Ribalta, Stuttgart (DE); Rainer Schluess, Bondorf (DE); Bernd Wilm, Rohrdorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1379 days.

(21) Appl. No.: 12/808,792

(22) PCT Filed: Dec. 8, 2008

(86) PCT No.: PCT/IB2008/055149
§ 371 (c)(1),
(2), (4) Date: Nov. 17, 2010

(87) PCT Pub. No.: WO2009/077915
PCT Pub. Date: Jun. 25, 2009

(65) Prior Publication Data
US 2011/0060234 A1    Mar. 10, 2011

Related U.S. Application Data

(60) Provisional application No. 61/014,613, filed on Dec. 18, 2007.

(51) Int. Cl.
*A61B 5/04* (2006.01)
*A61B 5/044* (2006.01)
*A61B 5/00* (2006.01)
*G06F 19/00* (2011.01)

(52) U.S. Cl.
CPC ....... *A61B 5/04011* (2013.01); *G06F 19/3406* (2013.01); *A61B 5/044* (2013.01); *A61B 5/7264* (2013.01); *A61B 5/7275* (2013.01)

(58) Field of Classification Search
CPC .... A61B 5/04; A61B 5/04011; A61B 5/044; A61B 5/7264; A61B 5/7275
USPC ............................. 600/509, 510; 607/9, 28
See application file for complete search history.

(56) References Cited

U.S. PATENT DOCUMENTS 5,419,337 A * 5/1995 Dempsey et al. ............ 600/515
5,819,741 A * 10/1998 Karlsson et al. ............. 600/523
5,827,195 A * 10/1998 Lander .......................... 600/509

(Continued)

FOREIGN PATENT DOCUMENTS

| WO | 2005046471 A | 5/2005 |
| WO | 2005072607 A | 8/2005 |
| WO | 2006033038 A | 3/2006 |

*Primary Examiner* — Christopher A Flory

(57) ABSTRACT

An ECG monitoring system analyzes ECG signals of leads associated with different anatomical locations of the body for evidence of ST elevation in the lead signals. The ST elevation and depression measurements of the leads are plotted in a graphical display organized in relation to the anatomical points which are the sources of the lead signals. The locations of the plotted measurements in the anatomically-oriented display indicate the identity of a specific coronary artery or branch as a possible culprit coronary artery for an acute ischemic event, as well as the possible severity of the event from the magnitudes of the plotted signals. A clinician can identify a suspect culprit coronary artery from a quick glance at the graphical display.

15 Claims, 17 Drawing Sheets

(56) References Cited

U.S. PATENT DOCUMENTS

| | | | |
|---|---|---|---|
| 5,891,045 A * | 4/1999 | Albrecht et al. | 600/509 |
| 6,038,469 A * | 3/2000 | Karlsson et al. | 600/512 |
| 6,171,256 B1 * | 1/2001 | Joo et al. | 600/508 |
| 6,217,525 B1 * | 4/2001 | Medema et al. | 600/508 |
| 6,381,493 B1 * | 4/2002 | Stadler et al. | 607/9 |
| 6,397,100 B2 * | 5/2002 | Stadler et al. | 600/509 |
| 6,501,983 B1 * | 12/2002 | Natarajan et al. | 600/517 |
| 6,609,023 B1 * | 8/2003 | Fischell et al. | 600/515 |
| 6,766,190 B2 * | 7/2004 | Ferek-Petric | 600/512 |
| 6,865,420 B1 * | 3/2005 | Kroll | 607/25 |
| 7,266,408 B2 * | 9/2007 | Bojovic et al. | 600/512 |
| 7,277,745 B2 * | 10/2007 | Natarajan et al. | 600/509 |
| 7,460,900 B1 * | 12/2008 | Gill et al. | 600/509 |
| 7,502,643 B2 * | 3/2009 | Farringdon et al. | 600/509 |
| 7,502,644 B2 * | 3/2009 | Gill et al. | 600/516 |
| 7,512,438 B2 * | 3/2009 | Fischell et al. | 600/509 |
| 7,697,974 B2 * | 4/2010 | Jenkins et al. | 600/428 |
| 7,844,323 B2 * | 11/2010 | Fischell et al. | 600/517 |
| 7,912,544 B1 * | 3/2011 | Min et al. | 607/9 |
| 7,949,388 B1 * | 5/2011 | Fong | 600/509 |
| 2003/0073914 A1 * | 4/2003 | Taha et al. | 600/509 |
| 2004/0138574 A1 * | 7/2004 | Groenewegen et al. | 600/509 |
| 2005/0085736 A1 * | 4/2005 | Ambrose et al. | 600/509 |
| 2005/0159666 A1 * | 7/2005 | Pearce et al. | 600/509 |
| 2006/0264770 A1 * | 11/2006 | Wellens et al. | 600/509 |
| 2008/0146954 A1 * | 6/2008 | Bojovic et al. | 600/512 |
| 2008/0194978 A1 * | 8/2008 | Beker et al. | 600/516 |
| 2009/0275846 A1 * | 11/2009 | Costa Ribalta et al. | 600/509 |
| 2010/0030034 A1 * | 2/2010 | Schulhauser et al. | 600/301 |
| 2011/0082350 A1 * | 4/2011 | Koh | 600/301 |
| 2012/0010515 A1 * | 1/2012 | Zhou et al. | 600/509 |

* cited by examiner

AUTOMATED IDENTIFICATION OF CULPRIT CORONARY ARTERY USING ANATOMICALLY ORIENTED ECG DATA DISPLAY

This invention relates to electrocardiographic (ECG) monitoring systems and, in particular, to real-time ST monitoring system which automatically identify, by means of an anatomically-oriented presentation, a culprit coronary artery which has caused an acute myocardial infarction.

Electrocardiography (ECG) is in widespread use to produce records derived from voltages produced by the heart on the surface of the human body. The records so produced are graphical in character and require expert interpretation and analysis to relate the resulting information to the heart condition of the patient. Historically, such records have been produced directly as visible graphic recordings from wired connections extending from the subject to the recording device. With advances in computer technology, it has become possible to produce such records in the form of digitally stored information for later replication and analysis.

An emergency clinical application where FOG records are critical is the diagnosis of symptoms of acute coronary disease, commonly referred to as heart attacks. Patients with acute coronary syndrome (ACS) such as chest pain or discomfort and shortness of breath are often diagnosed electrocardiographically, where the elevation or depression of the ST segments of ECG waveforms are critically analyzed. One scenario that frequently occurs is that the ST elevation of a patient's ECG at the time of admission to an emergency department or a chest pain center of a hospital does not meet the diagnostic criteria for a definitive ST elevation myocardial infarct (STEMI) diagnosis. In such cases, patients are often connected to an ECG monitor for ST segment monitoring to observe the progression or regression of ST variation, particularly with patients with a history of acute coronary syndrome (ACS). If the patient's condition deteriorates, the clinical caregiver responsible for the patient needs to know the coronary artery and the region of the myocardium at risk before intervention can proceed.

Another scenario is that an ACS patient is definitively diagnosed with an ECG presentation of STEMI, and undergoes interventional reperfusion therapy. Proven therapies to restore myocardial reperfusion include thrombolytics or percutaneous coronary intervention to open the infarct-related artery. Coronary artery bypass graft (CABG) is another perfusion therapy often applied to ACE patients with more serious occlusions. After the interventional procedure and during the thrombolytic therapy, the patient is usually connected to an ECG monitor for ST monitoring and observation in a recovery room, intensive care unit (ICU) or cardiac care unit (CCU) for observation of regression or progression of the patient condition. New episodes of coronary artery occlusion may occur if the previously cleared coronary artery becomes clotted again or an occlusion occurs in a different artery or the ST deviation will return to normal when the patient's coronary perfusion is restored. Since the first sixty minutes are critical for salvage of the myocardium, it is critical that clinical personnel capture the recurrence episodes early to prevent further damage to the myocardium.

The ST monitoring commonly performed in these scenarios has limitations, however. Episodes with ST elevation or ST depression are often missed due to use of a limited number of electrodes. Hospitals have widely varying protocols for lead availability and lead systems used in ST monitoring. Some hospitals use one channel (3 wire) ECG monitors, some use three channel (5 wire) systems, while others use five channel (six wire) systems, or twelve leads derived from five or six channel systems or calculated from a direct recording of eight channels. ST monitor design is often not intuitive for general clinical caregivers who may not have adequate training to understand the relationship between ECG leads and the associated myocardial regions or coronary arteries. Numeric changes or waveforms of ST segments displayed on bedside monitors do not have indications of corresponding relationships between each lead and the myocardial region at risk. Accordingly improved ECG monitors and protocols would improve the standard of care in these situations.

An ECG monitoring system which provides improved care in these situations is described in U.S. provisional patent application Ser. No. 60/954,367 entitled "AUTOMATED IDENTIFICATION OF CULPRIT CORONARY ARTERY (Zhou et al.), filed Aug. 7, 2007. The ECG monitor described in this patent application analyzes the ST segments of ECG waveforms produced by leads associated with different regions of the body. On the basis of the ST elevation and depression exhibited by different groups of leads, the system identifies to a clinician the coronary artery which is the likely location of an occlusion, the "culprit" coronary artery. The system does this using standard ECG lead placement and multiple ECG waveform presentation. While such a display provides all of the relevant diagnostic information for a definitive diagnosis, including an indication of the culprit artery, significant skill in the interpretation of ECG waveforms is still, necessary to relate the ECG data to the culprit artery indicated by the system. It would be desirable to have a graphical way of relating the ECG data to the diagnostic indication, so that the clinician could immediately appreciate the validity of the diagnostic determination before undertaking his or her own more detailed waveform analysis. The shorter the time to a definitive diagnosis, the sooner that myocardial perfusion can be restored, with less damage to the heart and a lower the risk for heart failure or death.

In accordance with the principles of the present invention, an ECG monitoring system is described which acquires ECG waveforms from a plurality of leads and analyzes the ST segment elevation and depression present. This ST segment information is presented in a graphical display which displays the information in relation to the anatomy of the patient. In an illustrated embodiment, the graphical display presents ST segment information in both a vertical (transverse) and a horizontal (lateral) orientation in relation to the lead positions which produced the information. The anatomically-oriented display shows at a glance an indication of the culprit coronary artery and the size of the myocardial region with the infarct or injury. The anatomically-oriented display may be produced in real time during monitoring, with comparison to a baseline condition, or in a time-lapsed display which indicates progression of the condition.

Figure 1:
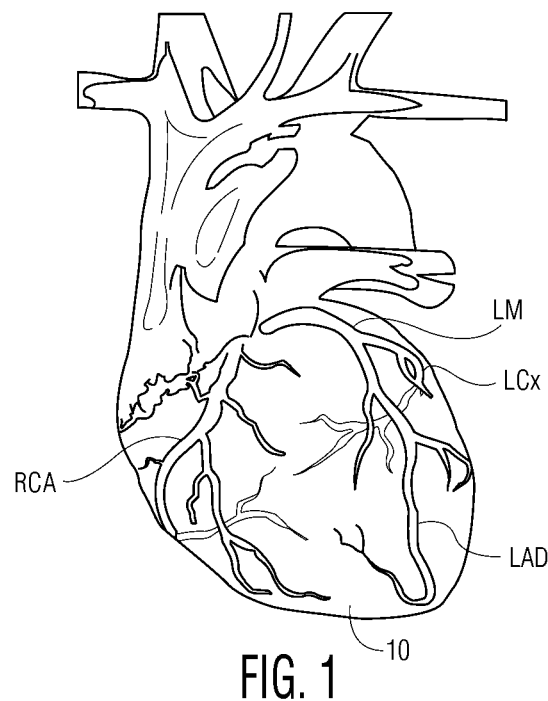
FIG. 1 is an anatomical illustration of the heart, showing the coronary arteries wrapping around the heart.

FIG. 1 is a view of the heart showing the locations of the coronary arteries which, when obstructed, will cause significant damage to the heart. In FIG. 1 the heart 10 is depicted as a translucent orb so that the tortuous paths of the coronary arteries on both the anterior and posterior surfaces of the heart can be readily visualized. The right coronary artery (RCA) is seen descending along the right side of the heart 10 from the aorta. Also descending from the aorta along the left side of the heart is the left main (LM) coronary artery, which quickly branches to form the left anterior descending (LAD) artery on the front (anterior) surface of the heart and the left circumflex (LCx) artery which wraps around the back (posterior) of the heart. All three major vessels are seen to ultimately wrap around the heart 10 in characteristic tortuous paths to provide a constant supply of fresh blood to the myocardium. When a patient is experiencing chest pain due to occlusion of one of the coronary arteries, it is important to quickly identify the arterial branch which is occluded so that intervention can be performed quickly to prevent damage to the heart.

Figure 2:
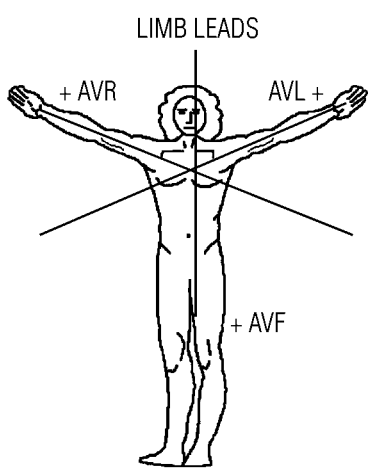
FIG. 2 is an illustration of the location of ECG limb leads in relation to a standing (vertical) individual.

FIG. 2 illustrates the limb leads of a typical ECG system and their relationship to the anatomy of the body. The limb lead signals and the other lead signals of an ECG system are produced by combining the outputs from specific electrodes attached at certain locations on the body. U.S. Pat. No. 6,052,615 (Feild et al.), for instance, shows how the lead signals are developed for a 12-lead ECG system. In the illustration of FIG. 2, the AVR lead relates to the right arm, the AVL lead relates to the left arm, and the AVE lead relates to the left leg of the body. When a person is standing as shown in the drawing, these three leads are in approximately a vertical (transverse) plane. For purposes of the present invention the lead signals have a polarity in relation to ST elevation above a nominal baseline as indicated by the "+" symbols in the drawing. At the opposite ends of the axes drawn along the respective limbs the lead signals have a negative connotation for ST elevation. This lead orientation and relationship will be discussed further below in connection with the various illustrations of displays of the present invention.

Figure 3A:
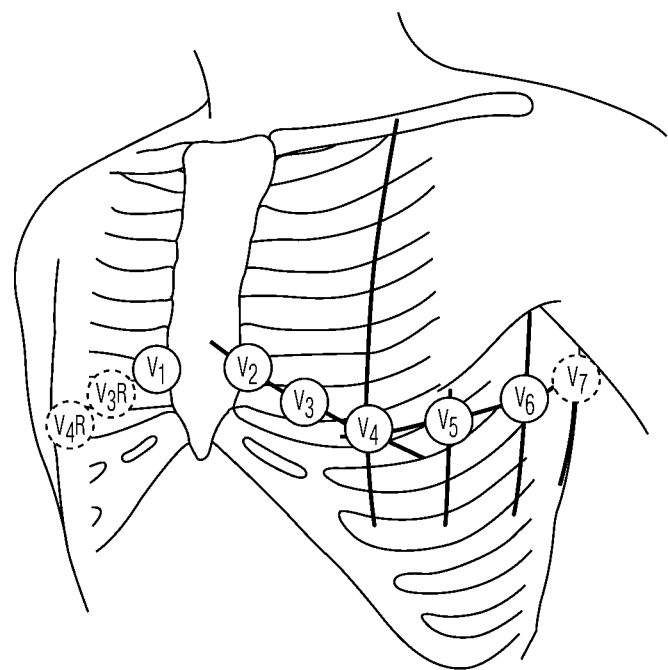
FIGS. 3a and 3b show standard chest electrode placement for an EGG exam.
Figure 3B:
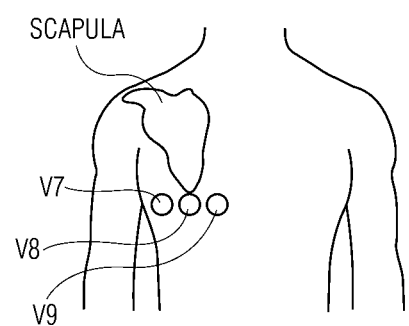

FIG. 3a shows the placement of six EGG chest electrodes V1-V6, which are located on the torso of the patient. FIG. 3b shows chest electrodes V7-V9 which continue around Lottie back (posterior) of the patient. As in the case of the limb electrodes, the signal of each chest electrode is used in combination with the signals of one or more other electrodes to detect voltages produced by depolarization and repolarization of individual heart muscle cells. For a 12-lead EGG system the detected voltages are combined and processed to produce twelve sets of time varying voltages. The tracings so produced are described in Feild et al. as follows:

| Lead | Voltage | Lead | Voltage |
| --- | --- | --- | --- |
| I | VL − VR | V1 | V1 − (VR + VL + VF)/3 |
| II | VF − VR | V2 | V2 − (VR + VL + VF)/3 |
| III | VF − VL | V3 | V3 − (VR + VL + VF)/3 |
| aVR | VR − (VL + VF)/2 | V4 | V4 − (VR + VL + VF)/3 |
| aVL | VL − (VR + VF)/2 | V5 | V5 − (VR + VL + VF)/3 |
| aVF | VF− (VL + VR)/2 | V6 | V6 − (VR + VL + VF)/3 |

The present invention is suitable for use with conventional 12-lead. EGG systems as well as with 13-, 14-, 15-, 16-, 17-, or 18-lead or greater systems, including 56- and 128-lead body surface mapping systems. Three-lead (EASI and other), 5-, and 8-lead systems can also be used to derive 12 leads, with reduced accuracy as is known in the art. See, for example, U.S. Pat. No. 5,377,687 (Evans et. al.) and U.S. Pat. No. 6,217,525 (Medema et al.) In sum, an implementation of the present invention can employ any number of leads and electrodes.

It can be seen that the chest electrode locations in FIGS. 3a and 3b are in approximately a horizontal plane with respect to a standing individual. As will be discussed below, this anatomical relationship also plays a role in the illustrated embodiments of the present invention.

Figure 4:
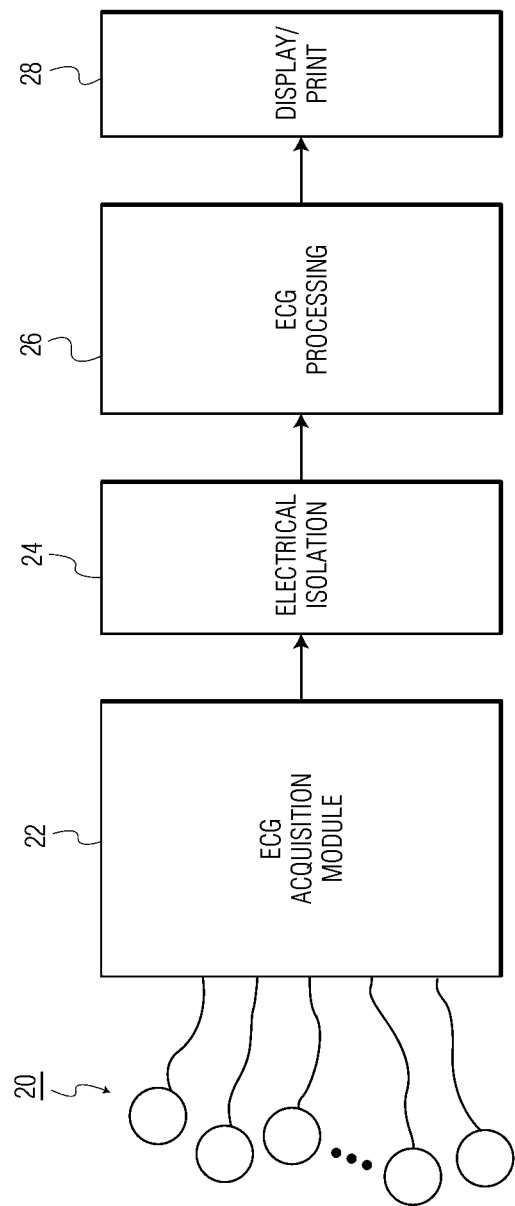
FIG. 4 is a block diagram of major subsystems of an ECG monitoring system suitable for use with the present invention.

FIG. 4 illustrates in block diagram form an ECG monitoring system suitable for use with the present invention. A plurality of electrodes 20 are provided for attaching to the skin of a patient. Usually the electrodes are disposable conductors with a conductive adhesive gel surface that sticks to the skin. Each conductor has a snap or clip that snaps or clips onto an electrode wire of the ECG system. The electrodes 20 are coupled to an ECG acquisition module 22 of the monitoring system that preconditions the signals received by the electrodes. The electrode signals are coupled to an ECG processing module 26, generally by means of an electrical isolation arrangement 24 that protects the patient from shock hazards and also protects the ECG system when the patient is undergoing defibrillation, for instance. Optical isolators are generally used for electrical isolation. The processed ECG information is then displayed on an image display or printed in an ECG report by an output device 28.

Figure 5:
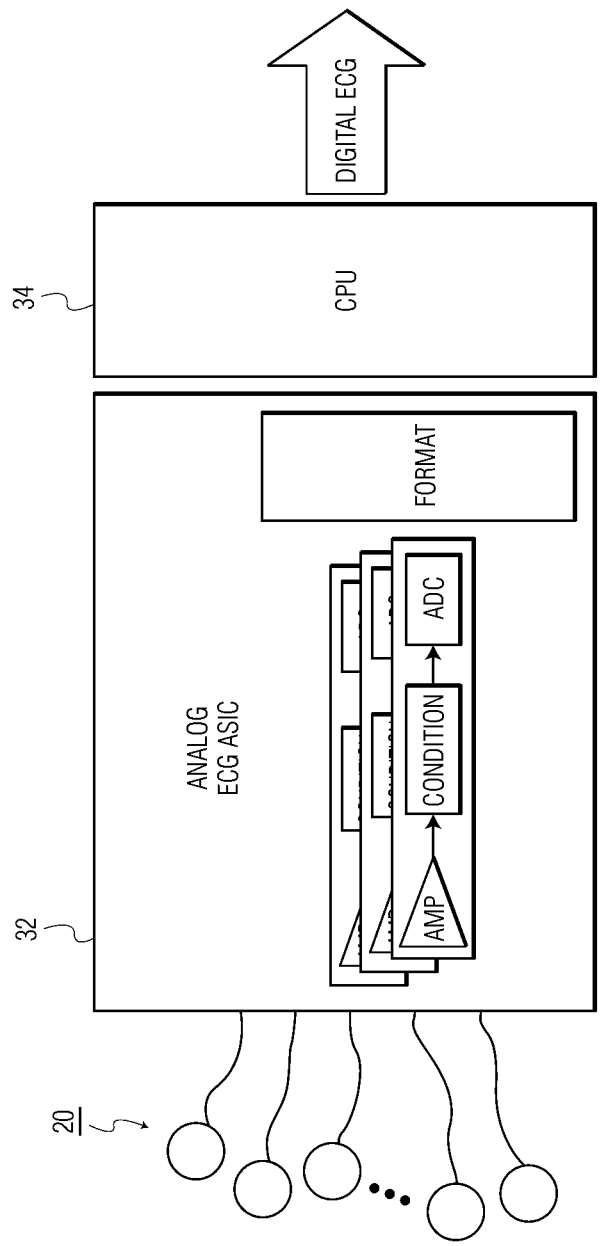
FIG. 5 is a block diagram of the front end of an ECG system.

FIG. 5 shows the acquisition module 22 in greater detail, starting with a signal conditioner 32. The electrode signals, which are usually just a few millivolts in amplitude, are amplified by amplifiers which also usually have high voltage protection from defibrillation pulses. The amplified signals are conditioned as by filtering and then converted to digitally sampled signals by analog to digital converters. The signals are then formatted by differentially combining various electrode signals to derive lead signals in combinations such as those given above for a 12-lead system. The digital lead signals are forwarded for ECG processing under control of CPU 34. Much of the specialized electronics of the acquisition module is often implemented in the form of an application-specific integrated circuit (ASIC).

Figure 6:
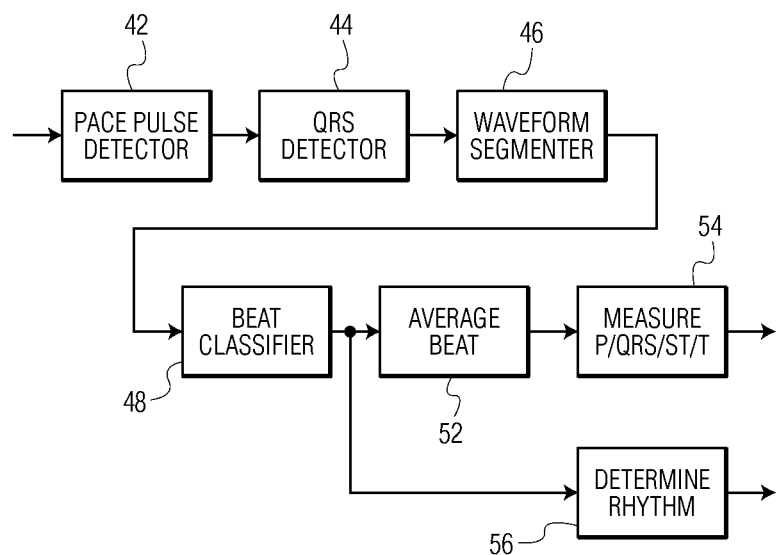
FIG. 6 is a block diagram of the processing module of a typical ECG monitor.
Figure 7:
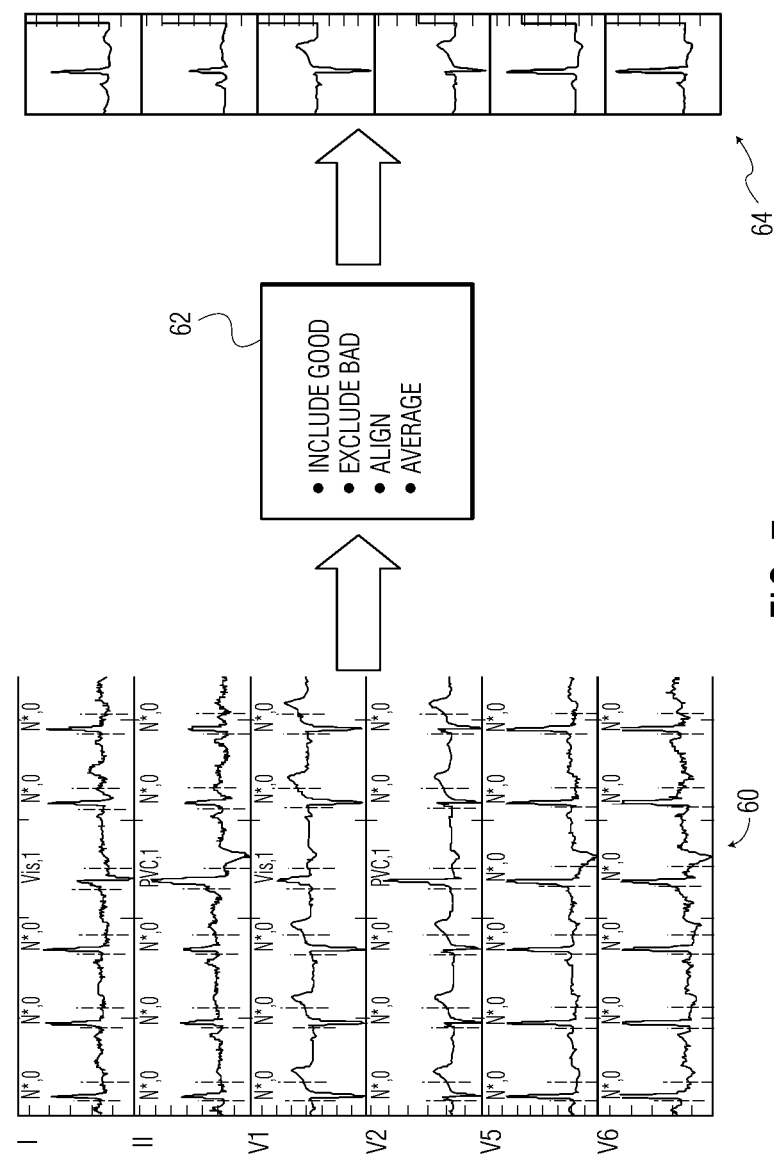
FIG. 7 illustrates the processing of ECG trace data to provide information about the heartbeat and its rhythm.
Figure 8:
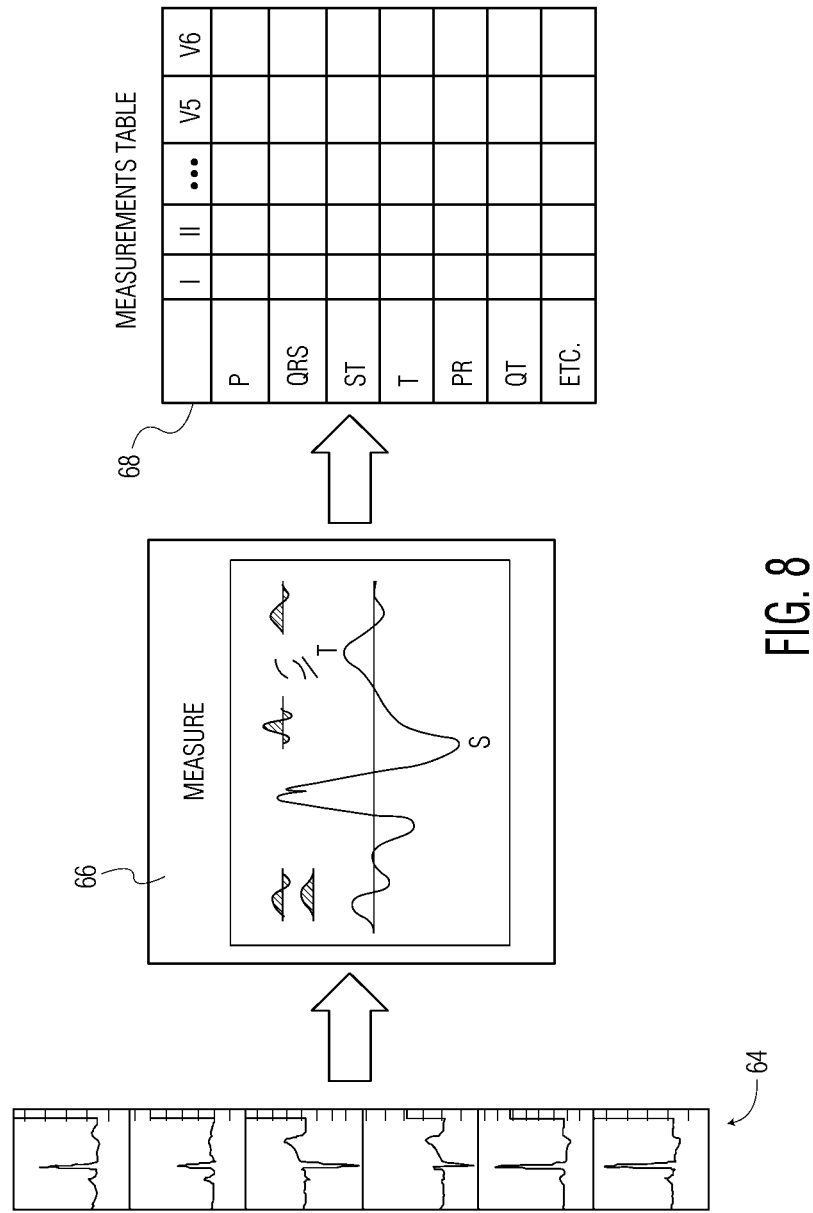
FIG. 8 illustrates the measurement of different parameters of an ECG trace.
Figure 9A:
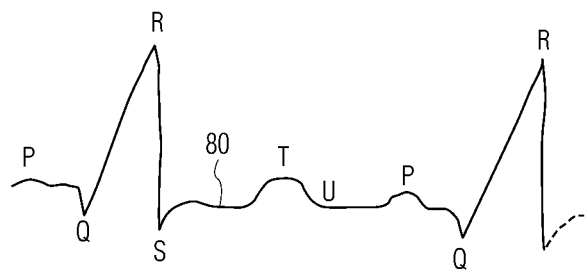
FIG. 9a illustrates the segments of a normal ECG signal.

FIG. 6 is a block diagram of the analysis portion of a typical diagnostic ECG system. A pace pulse detector 42 identifies and sets aside electrical spikes and other electrical abnormalities produced by a pacemaker for patients who are wearing one. A QRS detector 44 detects the dominant pulse of the electrical traces. FIG. 9a illustrates a typical normal ECG trace, where it is seen that the Q-R-S segments delineate the major electrical pulse of the trace, which is the pulse that stimulates a contraction of the left ventricle. Delineation of the QRS complex forms the basis for detecting the lesser perturbations of the trace, which is performed by the waveform segmenter 46. The waveform segmenter delineates the full sequence of trace segments including the P wave and the Q to U segments of the ECG trace including the S-T segment. With each waveform now fully delineated, a beat classifier 48 compares each new beat with previous beats and classifies beats as normal (regular) or abnormal (irregular) for the individual undergoing diagnosis. The classification of the beats enables an average beat analyzer 52 to define the characteristics of a normal heartbeat and the amplitudes and segment durations of an average beat are measured at 54. The beat classifications are used to determine the heart rhythm at 56. FIGS. 7 and 8 are functional illustrations of some of this ECG trace processing. At the left side of FIG. 7 is a series 60 of ECG traces from leads I, II, V1, V2, V5 and V6. The beat classifier 48 compares the various beat characteristics and has classified some of the beats as normal (N*,0). For example, all of the beats from leads V5 and V6 have been classified as normal. The other four leads contain a beat exhibiting the characteristics of premature ventricular contraction (PVC, 1) in this example. At 62 the ECG system aggregates the characteristics of the normal beats, excludes characteristics of the abnormal beats, aligns the beats in time and averages them to produce an average beat. The traces at 64 illustrate the traces of an average beat for the six leads shown in this example. In FIG. 8 the average beat traces 64 of the six leads are measured for various characteristics shown at 66, such as the amplitudes and durations of the Q wave, the R wave, and the T wave and inter-wave intervals such as ORS, ST, and QT. The measurements are illustrated as recorded in a measurement table 68 for the six leads of this example. The ECG waves and their measurements can be sent to an offline workstation with a report generation package for the production of a report on the patient's ECG waveforms. However most diagnostic ECG systems such as the Philips Pagewriter® line of cardiographs and the Philips TraceMaster® ECG management system have onboard ECG reporting packages.

Figure 9B:
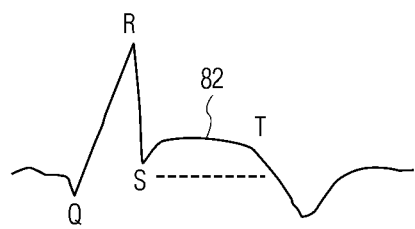
FIGS. 9b-9e illustrate ECG traces with elevated and depressed ST segments which may be used to produce an anatomically-oriented graphical display for culprit coronary artery identification in accordance with the principles of the present invention.
Figure 9C:
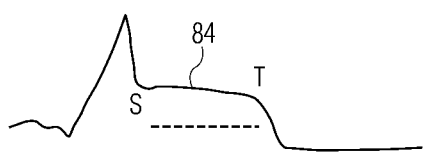
Figure 9D:
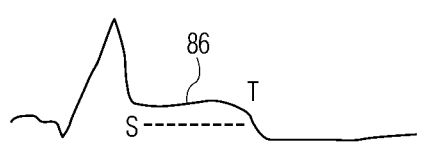
Figure 9E:
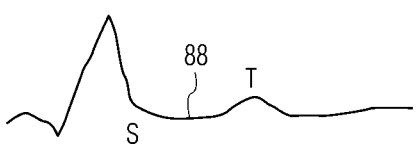

In accordance with a further aspect of the present invention, ECG lead signals are analyzed for particular patterns of elevated and depressed. ST segments which relate to stenoses of specific coronary arteries and branches. In the normal ECG trace of FIG. 9a, the signal level of the ST segment 80 is at or very close to the nominal baseline of the EGG trace. When a coronary artery becomes fully occluded, the ST segment 82 for a lead in proximity to the artery will be highly elevated as shown in FIG. 9b, where the dashed line indicates the nominal baseline of the trace. The ST segment can be elevated 100 volts or more. EGG leads proximate to the other side of the heart will exhibit a corresponding depression, which can be detected and correlated with the elevated trace for correlating identification of the ST elevation. Furthermore, the amount of ST elevation will vary as a function of the time and degree of stenosis. For example, shortly after the time of the event causing the obstruction, the ST segment of a lead will exhibit a relatively significant elevation 84 as shown in FIG. 9c. With the passage of time the elevation will decrease, and the ST elevation. 86 can appear as shown in FIG. 9d. After a substantial period of time, as the heart begins adapting to its new physiological condition, or when an artery is only partially occluded, the ST segment will be only slightly elevated or depressed as shown at 88 in FIG. 9e. ST depression is present when the ST segment is below the nominal baseline of the waveform. Thus, by querying the patient as to the time of onset of the chest pain the time of the event can be noted and the expected degree of elevation assessed. The degree of elevation can also be used to recognize only partially occluded vessels such as those in which an old blood clot has calcified over time. These indications can be used to set aside vessels not needing immediate attention while the interventional procedure is directed to the vessel which has just suffered major obstruction.

In accordance with the principles of the present invention, one of the present inventors has studded the statistical analyses of ECG databases and their relationship to different coronary artery anatomies and has participated in the development of an automated technique to identify the culprit artery of an acute ischemic event as described more fully in the previously referenced Zhou et al. patent application, the contents of which are incorporated herein by reference. This inventive technique can identify one of the two main coronary arteries, the RC and the LM, or one of the two main branches of the LM, the LEA or the LCx, as the culprit artery. The cardiologist is then informed of the identity of the culprit artery as by identifying it in the ECG report, visually on a screen, on a display of ECG traces, audibly, or by other output means. The other inventors have developed an inventive display technique for monitored ECG information as described in international publication number WO 2006/033038 (Costa Ribalta at al.) which is incorporated herein by reference. This display technique presents monitored data in a way that allows rapid detection of data in its spatial situation. Two and three dimensional graphical illustrations are presented in this patent publication. The illustrated graph displays give information not only about the current values of ST segment data but also about the spatial arrangement of the data. In accordance with the present invention, the present inventors have incorporated aspects of all of these developments to provide an EGG system which presents an anatomically-oriented graphic of ECG data from which a clinician can quickly identify a culprit coronary artery which is occluded and a possible cause of an acute ischemic event. A monitoring system of the present invention can be used with a patient with chest pain who has just arrived at a hospital and needs an initial diagnosis, as well as with patients who have undergone intervention and who are being monitored for further coronary artery occlusions or abnormalities.

Figure 10:
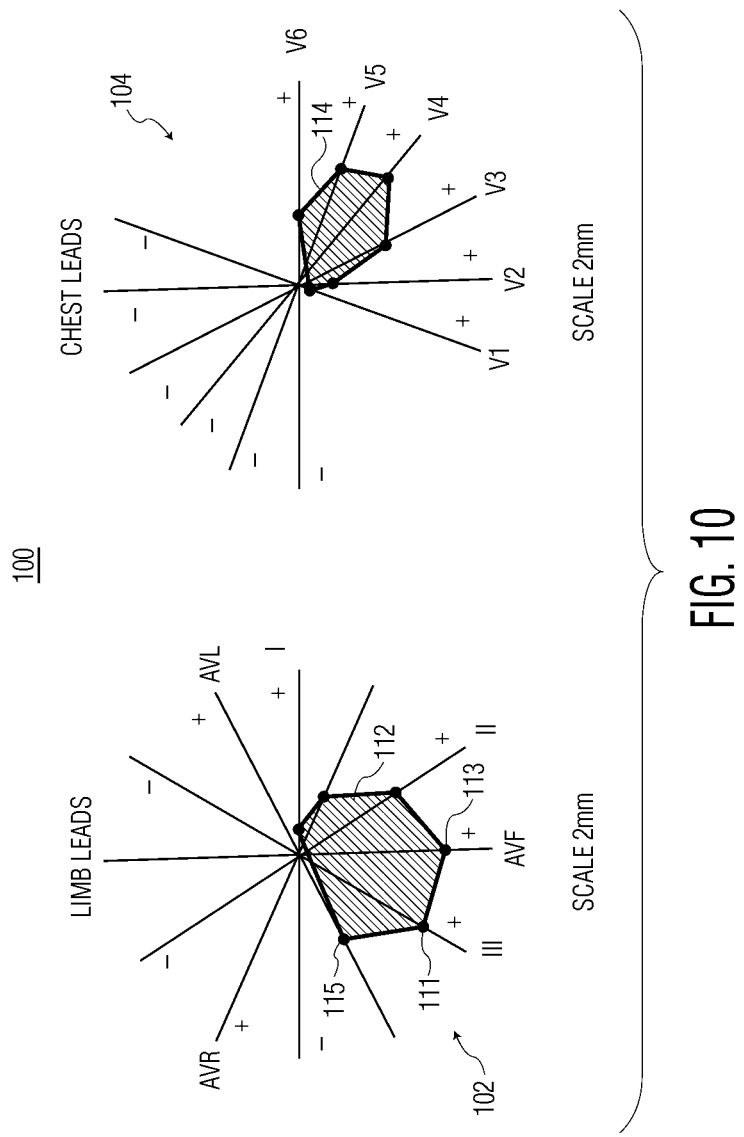
FIG. 10 illustrates an anatomically-oriented graphical display for culprit coronary artery identification in accordance with the principles of the present invention.

Referring now to FIG. 10, a display 100 of the type described in Costa Ribalta et al. is shown. The graphic 102 on the left uses the limb leads which, as previously mentioned are approximately in a vertical plane. In addition to the AVR, AVL and AVF leads shown in FIG. 2, the graphic 102 uses the I, II, and III leads which are also developed from limb electrode signals. The graphic includes axes for the signals which are oriented in relation to the limb positions shown in FIG. 2, with axis for the I lead being the horizontal (0°) axis in the drawing and the II and III lead axes disposed on opposite sides of the vertical (90°) AVF axis. In this example the ends of the axes are scaled to 2 mm of ST elevation, the millimeter notation being familiar to most cardiologists. The translation from the electrical units measured by the Lou system to toe millimeter notation is 100 μvolts equals 2 millimeters.

The axes in the graphic 102 are also seen to have + and − polarities. A lead exhibiting an ST elevation will have the data value plotted on the positive side of the axis from the origin, and ST depression measurements are plotted on the remaining negative side of the axis. The graphic 102 is seen to have six. ST data values plotted on the axes of the graphic. The value of point 111 on the axis for the II lead, for example, is near the positive end of the axis. This is an ST elevation value approaching 2 mm in the scale of this drawing. The ST elevation value of the AVF lead is also approaching 2 mm as shown by point 113 near the + end of the AVF axis. The point 115 plotted on the AVL axis is seen to be on the negative, side of that lead axis. In this example point 115 shows that ST depression of approximately 1 mm is present on the AVL lead.

The points plotted on the lead axes are connected by lines and the area inside the lined shape 112 is colored or shaded as shown in the drawing. Thus, the clinician can see at a glance that the plotted ST values delineate a sizeable shape 112 centered at the bottom of the graphic.

A similar graphic 104 is provided for the chest leads as shown at the right side of the display 100. In this example axes for the chest leads are arrayed from V1 through V6 in the same order as they are physically oriented on the chest. In this example the V1 axis is located at approximately the 112° position of the polar graphic and the other lead axes proceed counter-clockwise from this position. While this example uses only the six leads on the front (anterior) of the chest (FIG. 3a), it will be appreciated that axes for the other chest leads V7-V9 which continue around the torso to the back of the chest as shown in FIG. 3b can also be included to further fill out the array of axes in the graphic 104. This (graphic 104 uses + and − polarities for the ST elevation and depression values in the same manner as graphic 102. The ST elevation and depression values are similarly plotted as points on the respective lead axes and the points connected to form a shape 114 in the same manner as graphic 102. Thus it is seen at a glance that the chest lead graphic 104 is presenting a slightly smaller shape 114 which is positioned in the lower right quadrant of the graphic, centered around the V4 lead location.

Figure 11:
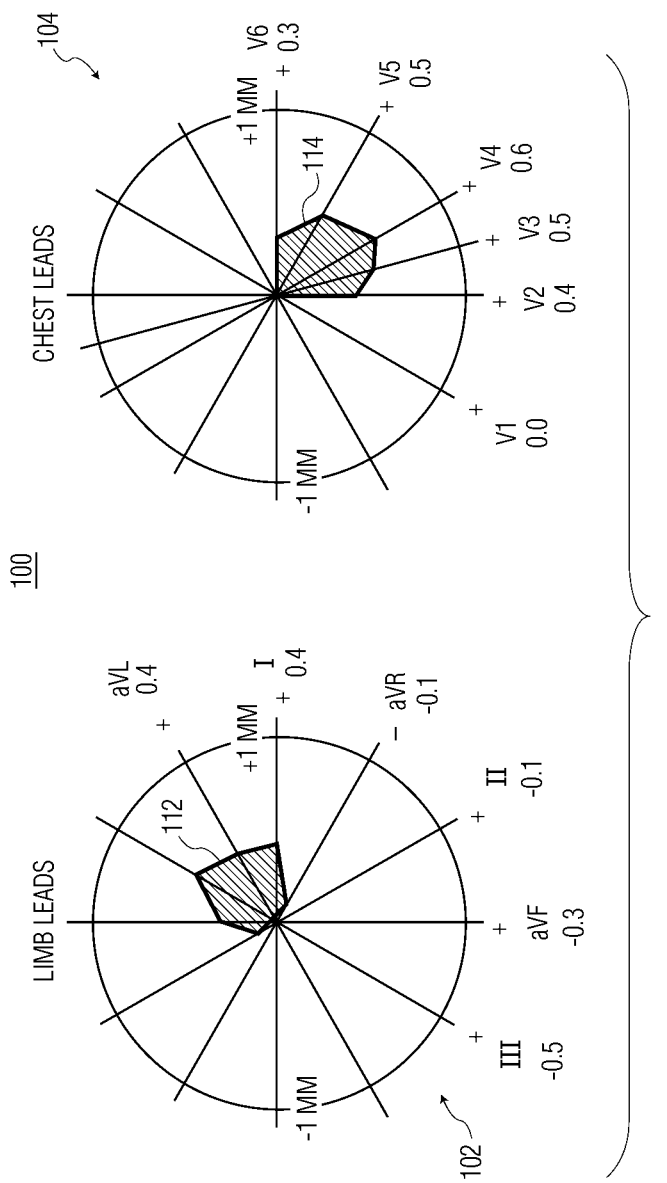
FIG. 11 illustrates a second anatomically-oriented graphical display, showing the ST segment values used to produce the display.

The display 100 of FIG. 11 is similar to that of FIG. 10 but has been drawn to shown the millimeter values of the ST segment measurements adjacent to the respective lead axes. For instance lead III is exhibiting ST depression of −0.5 mm, which is plotted on the negative side of the III lead axis and defines the greatest extension of the shape 112 from the origin of the polar graphic. The chest lead V4 with a measured ST elevation of 0.6 mm defines the greatest extension of the shape 114 from the origin of the chest lead graphic 104. It is seen that the axes in this example are scaled to a maximum extension of ±1 mm.

In accordance with the principles of the present invention, the locations of the ECG-derived shapes in the anatomically related graphics are used to visually identify suspect culprit coronary arteries. In the limb lead graphic 102 an ECG-derived shape which is located in the region indicated by the circled LAD will generally be symptomatic of: obstruction of the left anterior descending (LAD) coronary artery. A shape located around the left center of the graphic is usually indicative of a right coronary artery obstruction as indicated, by the circled RCA. Obstruction of the left circumflex coronary artery is signaled by a shape located around the bottom center of the graphic as indicated by the circled LCx. The locations of ECG-derived shapes signaling possible LCx, RCA, and LAD obstruction are similarly shown in the chest lead graphic 104 by the circled letters. The graphic 104 shows an ST segment-delineated shape in the lower right quadrant of the graphic, indicative of obstruction of the left anterior descending coronary artery. It is seen that a clinician can take a quick look at the display 100 and immediately see which coronary artery is the probably cause of an ischemic condition.

Figure 13:
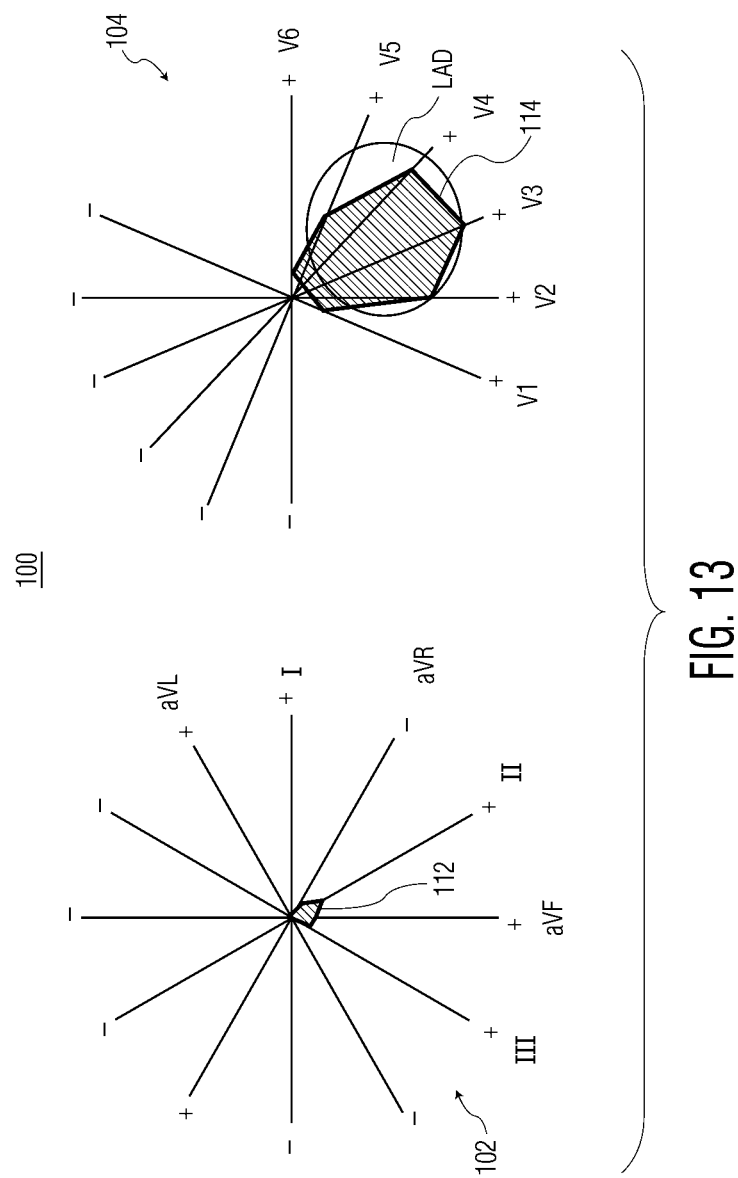
FIG. 13 is an example of an anatomically-oriented graphical display of the present invention indicating occlusion of the left anterior descending (LAD) coronary artery.

The examples below are of anatomically oriented displays indicating obstruction of particular coronary arteries. In FIG. 13 the plotted ST elevation values of the chest leads in the horizontal graphic 104 delineate a sizeable shape 114 in a location of the graphic that is characteristic of LAD occlusion. The limb lead (vertical) graphic 102 shows only a very small shape 112 near the origin of the graphic, showing that virtually no ST elevation or depression has been measured by the limb leads. This display 100 would suggest to a clinician that the LAD is the culprit coronary artery.

Figure 14:
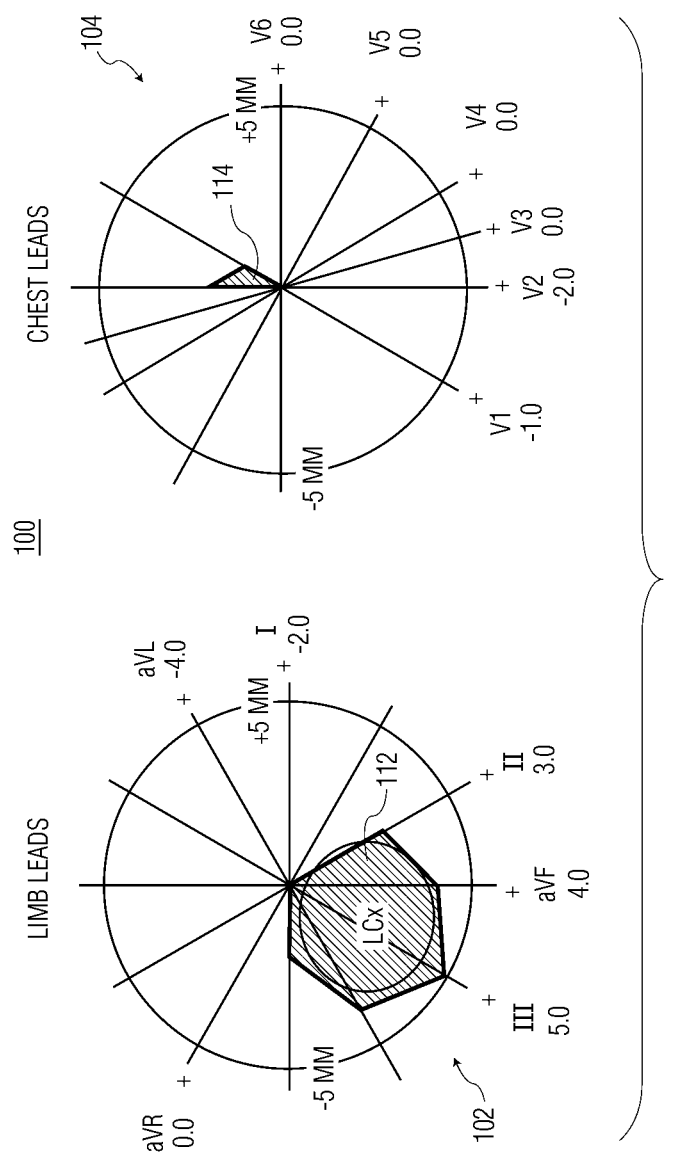
FIG. 14 is an example of an anatomically-oriented graphical display of the present invention indicating occlusion of the left circumflex (LCx) coronary artery.

FIG. 14 illustrates a display 100 showing both the lead axes and the respective ST elevation or depression measurements plotted on those axes. A sizeable shape 112 is formed in the limb lead graphic 102 by the significant ST elevation values measured for leads II, III, and aVF, and the ST depression values measured for leads I and aVL. Very little ST depression is measured by the chest leads as shown by the small shape 114 in the chest lead graphic 104. As the drawing indicates, the large shape 112 in the lower left quadrant of the limb lead graphic 102 would suggest obstruction of the left circumflex (LCx) coronary artery.

Figure 15:
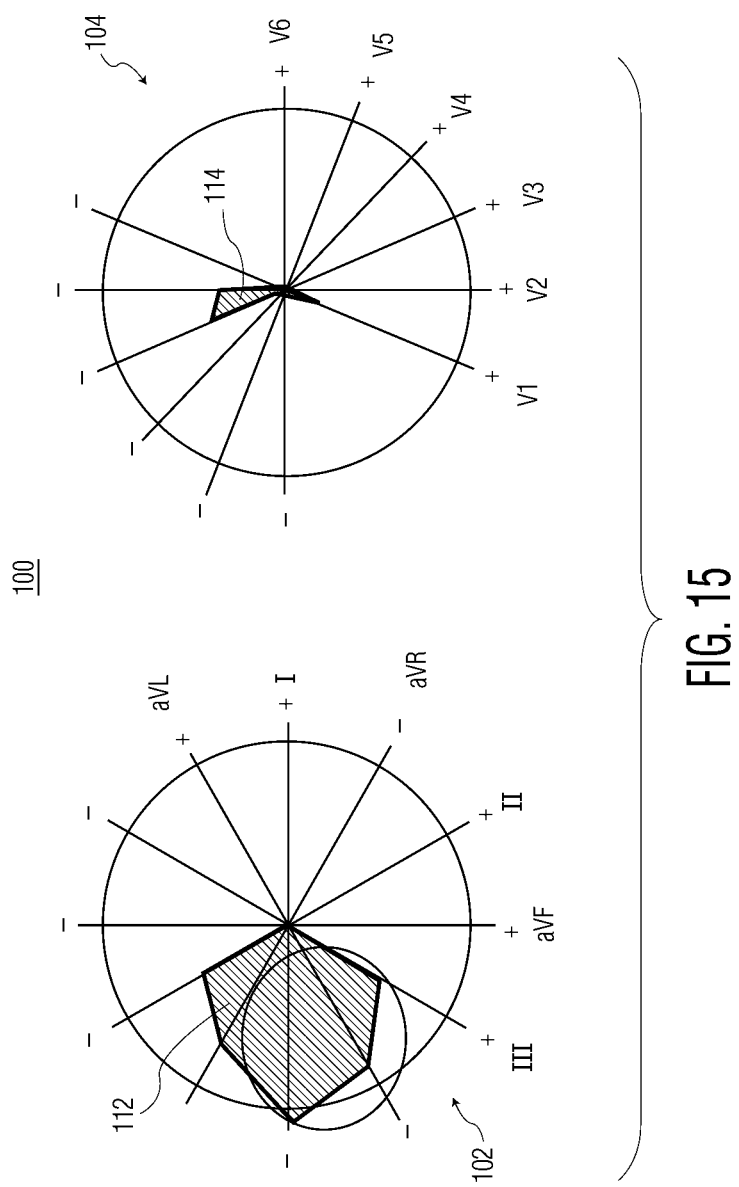
FIG. 15 is an example of an anatomically-oriented graphical display of the present invention indicating occlusion of the right coronary artery (RCA).

FIG. 15 shows a sizeable shape 112 delineated by ST elevation and depression measurements made at the limb leads and used in the limb lead graphic 102. The location of the shape 112 at the left side of the graphic 102 corresponds to the right side of the patient's anatomy (see FIG. 2). The small shape 114 in the chest lead graphic 104 indicates virtually no ST elevation measured by the chest leads; only slight ST depression. The shapes 112,114 of this display 100 are suggestive of a right coronary artery (RCA) obstruction as indicated by the circled letters over the shape 112.

Figure 16:
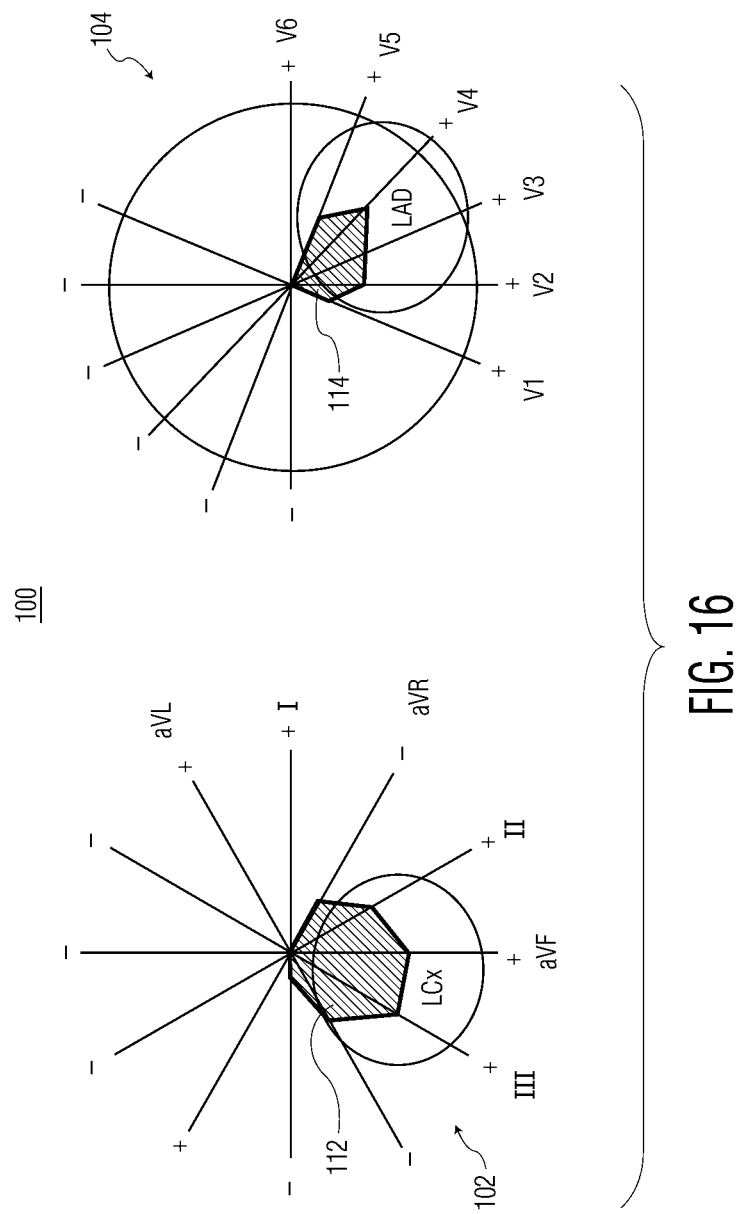
FIG. 16 is an example of an anatomically-oriented graphical display of the present invention indicating occlusion of both the left circumflex and the left anterior descending coronary arteries.

FIG. 16 is an example of a display 100 which suggests that two coronary arteries are suspect. The shape 112 of the ST elevation data measured by the limb leads in the vertical lead graphic 102 suggests a possible occlusion of the LCx coronary artery. The shape 114 produced by the ST elevation data used in the chest lead graphic 104 is suggestive of a possible occlusion of the LAD coronary artery. This display visually gives the clinician a quick indication that multiple coronary arteries should be examined more closely for possible occlusion.

Figure 17:
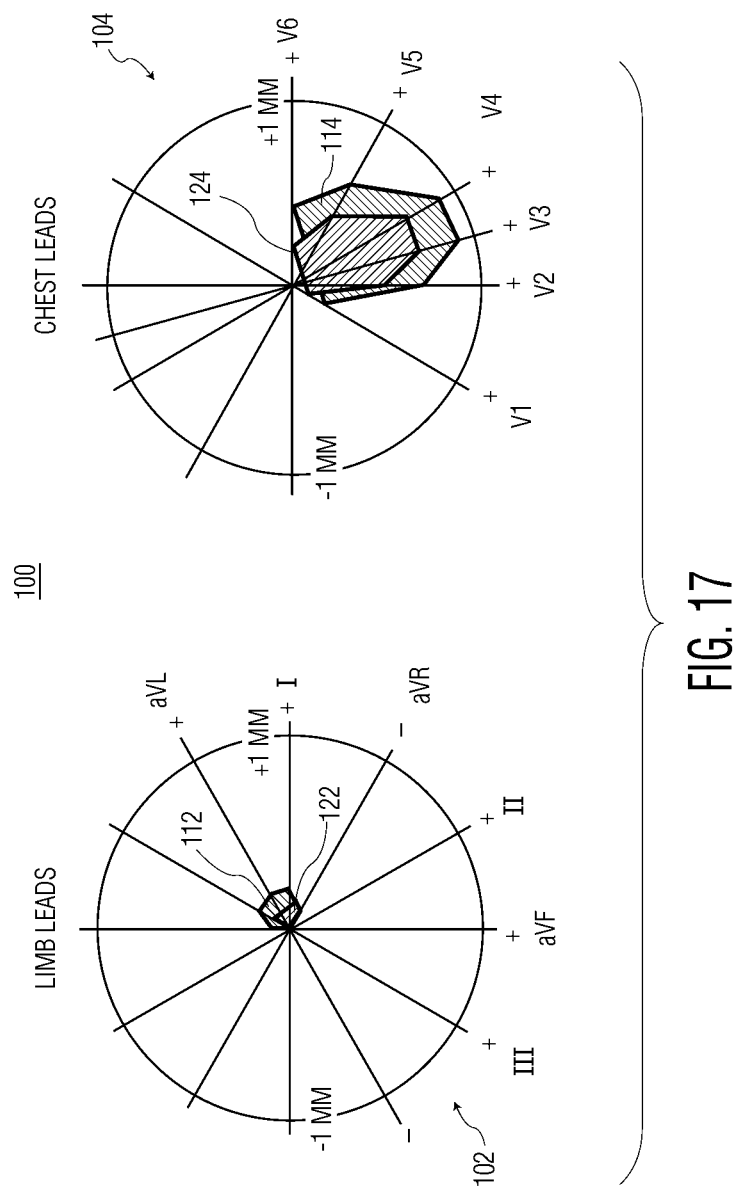
FIG. 17 illustrates an anatomically-oriented graphical display of the present invention in which the current ST elevation and depression characteristics are compared to baseline characteristics.

FIG. 17 is an example of another implementation of the present invention in which the progression of the patient's condition can be monitored. Such an embodiment would be useful, for instance, for a patient upon admission to the hospital with chest pain, when the clinician wants to now if the signs of possible ischemia are increasing. In this display 100 each of the graphics 102,104 shows an outline 122,124 of the shape delineated by ST elevation measurements made at the time that the patient was first connected to the ECG system electrodes. These initial outlines 122,124 may be shown constantly on the display 100 or may be recalled by the clinician. Also shown on the limb lead and chest lead graphics 102,104 are shapes 112,114 delineated by the most current FOG measurements made by the EGG system. By comparing the initial and current shapes 122,124 and 112, 114 on the display, the clinician can see at a glance whether the indications of coronary occlusion are increasing, declining, or remaining the same. In this example the shapes 112,114 of the most current measurements are noticeably larger than those of the measurements at the time of admission to the hospital, indicating the possibility of a worsening ischemic condition.

Figure 12:
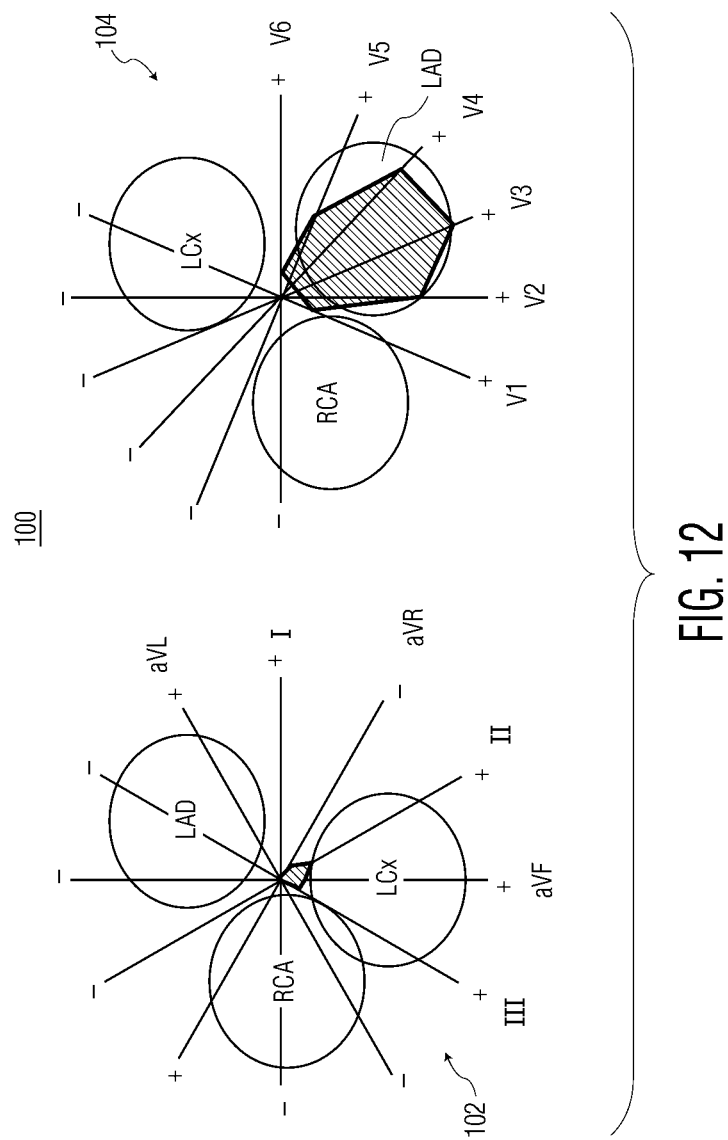
FIG. 12 illustrates the identification of a culprit coronary artery by means of an anatomically-oriented graphical display in accordance with the principles of the present invention.
Figure 18:
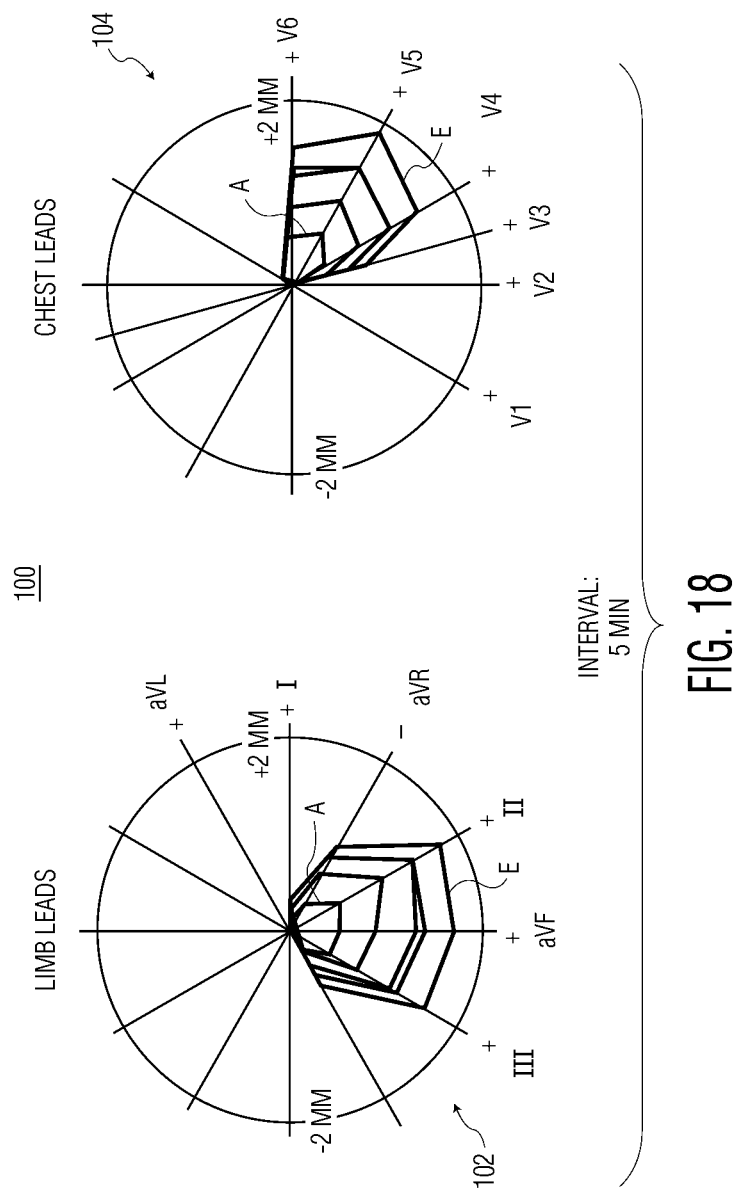
FIG. 18 illustrates an anatomically-oriented graphical display of the present invention in which the trend of ST elevation and depression characteristics over time is presented.

FIG. 18 is another example of an embodiment for monitoring the progress of the patient's condition over time. In this embodiment ST elevation is measured at periodic intervals, in this example, every five minutes. Each time a measurement is made, the outline A, . . . E of the shape delineated by the ST elevation measurements at that time is retained, on the display or saved to be called up and displayed as desired. In this example the five successive outlines A, . . . E acquired over time and displayed in the limb lead graphic 102 show a progression indicating an increasingly deteriorating condition of LCx occlusion (see FIG. 12). The five successive outlines A, . . . E displayed in the chest lead graphic 104 indicate a possible progression of LAD coronary artery occlusion. The simultaneous display of the successively produced outlines immediately depict trends of the patient's condition over time. The different outlines may be differently drawn or colored on the display for ease of interpretation.

While the foregoing examples are of displays with two two-dimensional (vertically and horizontally oriented) graphics, it will be appreciated that this information can be combined vectorially into a single graphic display, or in a single three-dimensional display which may be examined and moved or rotated (e.g., dynamic parallax) by the operator to present a three-dimensional impression of coronary artery defects.

In addition to the ST elevation and depression characteristics described above, other FOG measurements such as amplitudes and durations of Q wave, R wave, T wave and interwave intervals such as QRS and QT may also be used as applicable in the identification of the culprit coronary artery. The use of higher order lead sets including 13- to 18-lead FOG systems and 64- and 128-lead ECG body surface maps can provide additional incremental information to enhance the accuracy of culprit coronary artery identification. For systems with fewer than 12 leads, additional lead signals can be derived to implement the technique of the present invention with potentially reduced accuracy. It will also be appreciated that thresholds of ST elevation can be used for different ages, genders, and leads which are determined by appropriate AMA guidelines or other criteria. The graphical display can be highlighted as by coloring or labeling the outlined areas with the identity of the suspected coronary artery when ST elevation measurements exceed the appropriate thresholds for a patient. For instance, an outlined area can be highlighted if a male patient between 30 and 40 years of age presents ST elevation in leads V2 and V3 of greater than 2.5 mm (250 μvolts) and ST elevation in excess of 1 mm (100 μvolts) for all other leads. For a female, the area would be highlighted if ST elevation in the critical leads exceeds 1.5 mm (150 μvolts). Other threshold criteria may be used as appropriate standards are developed.

What is claimed is:

1. An ECG monitoring system which identifies a culprit coronary artery in a subject patient heart associated with an acute myocardial infarction comprising:

a set of electrodes adapted for acquisition of electrical activity of the heart from different vantage points in relation to the heart;

an ECG acquisition module coupled to the electrodes which acts to produce enhanced electrode signals;

an ECG processor responsive to the electrode signals which acts to combine electrode signals for the production of a plurality of lead signals measuring electrical activity of the heart from different vantage points, wherein the ECG processor detects ST elevation in lead signals; and a display responsive to detected ST elevation which displays each of a plurality of ST elevation data graphically in relation to anatomical lead locations, wherein the graphical display indicates the identity of a suspect culprit coronary artery or branch associated with an acute ischemic event.

2. The ECG monitoring system of claim 1, wherein the set of electrodes comprises a set of chest electrodes, wherein the ECG acquisition module acts to produce enhanced chest electrode signals, and further wherein the ECG processor is responsive to a plurality of chest electrode signals for the production of ST elevation data and use of the data for the production of a chest graphic showing the ST elevation data in a plane that is oriented horizontally with respect to the anatomy of a standing subject, wherein the chest graphic is indicative of one or more of left circumflex (LCx), right coronary artery (RCA), and left anterior descending (LAD) coronary artery occlusion.

3. The ECG monitoring system of claim 2, wherein the chest graphic further comprises a shape delineated by ST elevation data values.

4. The ECG monitoring system of claim 3, wherein the shape is formed by connecting ST elevation data values in the chest graphic.

5. The ECG monitoring system of claim 3, wherein the ECG processor is responsive to the plurality of chest electrode signals for the production of ST depression data, and further wherein ST elevation data values are located with one polarity in the chest graphic, and ST depression data values are located with an opposite polarity in the chest graphic.

6. The ECG monitoring system of claim 1, wherein the set of electrodes comprises a set of limb electrodes, wherein the ECG acquisition module acts to produce enhanced limb electrode signals, and further wherein the ECG processor is responsive to a plurality of limb electrode signals for the production of ST elevation data and use of the data for the production of a limb lead graphic showing the ST elevation data in a plane that is oriented vertically with respect to the anatomy of a standing subject, wherein the limb lead graphic is indicative of one or more of left circumflex (LCx), right coronary artery (RCA), and left anterior descending (LAD) coronary artery occlusion.

7. The ECG monitoring system of claim 6, wherein the limb lead graphic further comprises a shape delineated by ST elevation data values.

8. The ECG monitoring system of claim 7, wherein the shape is formed by connecting ST elevation data values in the limb lead graphic.

9. The ECG monitoring system of claim 7, wherein the ECG processor is responsive to the plurality of limb electrode signals for the production of ST depression data, and further wherein ST elevation data values are located with one polarity in the limb lead graphic, and ST depression data values are located with an opposite polarity in the limb lead graphic.

10. A method of operating an ECG monitoring system having a plurality of leads to identify a culprit coronary artery in a subject associated with an ischemic event comprising:
    receiving ECG signals of the plurality of leads associated with different anatomical locations of the subject chest and limbs;
    analyzing the ECG signals for ST elevation data;
    displaying each of a plurality of the ST elevation data graphically in relation to anatomical locations of the subject; and
    identifying from the graphical display a specific coronary artery or branch as a culprit coronary artery.

11. The method of claim 10, wherein analyzing further comprises analyzing the ECG signals for ST elevation data and ST depression data;
    wherein displaying further comprises displaying the ST elevation data and the ST depression data graphically in relation to anatomical locations of the subject.

12. The method of claim 10, wherein displaying further comprises displaying a first graphic containing ST elevation data associated with limb leads and displaying a second graphic containing ST elevation data associated with chest leads.

13. The method of claim 12, wherein the first and the second graphics each further comprises a shape delineated by ST elevation data,
    wherein the location of the shape in the graphic identifies a specific coronary artery or branch as a culprit coronary artery.

14. The method of claim 10, wherein analyzing further comprises comparing ST elevation data to a threshold.

15. A method of operating an ECG monitoring system having a plurality of leads to monitor the progression of a symptom of a culprit coronary artery in a subject associated with an ischemic event comprising:
    receiving ECG signals of the plurality of leads associated with different anatomical locations of the subject chest and limbs;
    analyzing the ECG signals for ST elevation data;
    displaying each of a plurality of the ST elevation data graphically in relation to anatomical locations of the subject;
    repeating the receiving and analyzing steps at least once at a later time;
    displaying the ST elevation data of the later time graphically and concurrently with the previously displayed ST elevation data; and
    identifying from the concurrent graphical display the progression of a symptom of coronary artery disease associated with a specifically identified coronary artery or branch.

* * * * *